US008137300B2

(12) United States Patent
Han et al.

(10) Patent No.: US 8,137,300 B2
(45) Date of Patent: Mar. 20, 2012

(54) ACCESS DISCONNECTION SYSTEMS AND METHODS USING CONDUCTIVE CONTACTS

(75) Inventors: James Han, Palm Harbor, FL (US); Thomas P. Hartranft, Clearwater, FL (US); Thomas D. Kelly, Tampa, FL (US); Angel Lasso, Tampa, FL (US)

(73) Assignees: Baxter International Inc., Deerfield, IL (US); Baxter Healthcare S.A., Glattpark (Opfikon) (CH)

(*) Notice: Subject to any disclaimer, the term of this patent is extended or adjusted under 35 U.S.C. 154(b) by 179 days.

(21) Appl. No.: 12/727,993

(22) Filed: Mar. 19, 2010

(65) Prior Publication Data
US 2010/0185132 A1 Jul. 22, 2010

Related U.S. Application Data

(63) Continuation of application No. 11/331,609, filed on Jan. 16, 2006, now Pat. No. 7,682,328, which is a continuation of application No. 10/120,684, filed on Apr. 10, 2002, now Pat. No. 7,052,480.

(51) Int. Cl.
*A61M 37/00* (2006.01)
*C02F 1/44* (2006.01)

(52) U.S. Cl. ............ 604/6.09; 604/5.04; 604/6.11; 210/645; 210/746

(58) Field of Classification Search ............ 604/5.04, 604/4.01, 6.06, 6.08, 6.09, 6.16, 5.01; 210/645, 210/646, 103, 85, 87, 746; 422/44; 73/861.08
See application file for complete search history.

(56) References Cited

U.S. PATENT DOCUMENTS

| | | |
|---|---|---|
| 3,309,924 A | 3/1967 | Kolin et al. |
| 3,682,162 A | 8/1972 | Colyer |
| 3,731,685 A | 5/1973 | Eidus |
| 3,759,261 A | 9/1973 | Wang |
| 3,778,570 A | 12/1973 | Shuman |
| 3,809,078 A | 5/1974 | Mozes |
| 3,810,140 A | 5/1974 | Finley |
| 3,814,249 A | 6/1974 | Eaton |
| 3,832,067 A | 8/1974 | Kopf et al. |
| 3,832,993 A | 9/1974 | Clipp |
| 3,867,688 A | 2/1975 | Koski |
| 3,882,861 A | 5/1975 | Kettering et al. |
| 3,900,396 A | 8/1975 | Lamadrid |
| 3,946,731 A | 3/1976 | Lichtenstein |
| 4,017,190 A | 4/1977 | Fischel |
| 4,022,211 A | 5/1977 | Timmons et al. |
| 4,026,800 A | 5/1977 | Friedrich et al. |
| 4,055,496 A | 10/1977 | Friedrich et al. |

(Continued)

FOREIGN PATENT DOCUMENTS
AU  199896231  3/1999
(Continued)

*Primary Examiner* — Leslie Deak
(74) *Attorney, Agent, or Firm* — K&L Gates LLP

(57) ABSTRACT

An extracorporeal blood system includes: an extracorporeal blood machine including an extracorporeal blood circuit; an access device enabling the extracorporeal blood circuit to be connected to a patient; first and second tube connecting members for connecting respectively to first and second tubes of the extracorporeal circuit; first and second electrodes held, at least in part, by the first and second tube connecting members so as to contact blood flowing through the extracorporeal blood circuit, the first and second electrodes enabling an electrical signal to be injected into the extracorporeal blood circuit; first and second contact members contacting the first and second electrodes respectively; and electronics coupled operably to the first and second contact members for applying the electrical signal, the signal used to monitor the access device.

18 Claims, 11 Drawing Sheets

U.S. PATENT DOCUMENTS

| | | |
|---|---|---|
| 4,085,047 A | 4/1978 | Thompson |
| 4,087,185 A | 5/1978 | Lamadrid |
| 4,162,490 A | 7/1979 | Fu et al. |
| 4,166,961 A | 9/1979 | Dam et al. |
| 4,181,610 A | 1/1980 | Shintani et al. |
| 4,191,950 A | 3/1980 | Levin et al. |
| 4,192,311 A | 3/1980 | Felfoldi |
| 4,193,068 A | 3/1980 | Ziccardi |
| 4,231,366 A | 11/1980 | Schael |
| 4,231,370 A | 11/1980 | Mroz et al. |
| 4,327,731 A | 5/1982 | Powell |
| 4,353,368 A | 10/1982 | Slovak et al. |
| 4,366,051 A | 12/1982 | Fischel |
| 4,484,573 A | 11/1984 | Yoo |
| 4,501,583 A | 2/1985 | Troutner |
| 4,534,756 A | 8/1985 | Nelson |
| 4,539,559 A | 9/1985 | Kelly et al. |
| 4,559,496 A | 12/1985 | Harnden, Jr. et al. |
| 4,583,546 A | 4/1986 | Garde |
| 4,648,869 A | 3/1987 | Bobo, Jr. |
| 4,661,093 A | 4/1987 | Beck et al. |
| 4,710,163 A | 12/1987 | Butterfield |
| 4,739,492 A | 4/1988 | Cochram |
| 4,740,755 A | 4/1988 | Ogawa |
| 4,792,328 A | 12/1988 | Beck et al. |
| 4,796,014 A | 1/1989 | Chia |
| 4,846,792 A | 7/1989 | Bobo, Jr. et al. |
| 4,862,146 A | 8/1989 | McCoy et al. |
| 4,898,587 A | 2/1990 | Castello |
| 4,936,834 A | 6/1990 | Beck et al. |
| 4,959,060 A | 9/1990 | Shimomura et al. |
| 4,965,554 A | 10/1990 | Darling |
| 4,976,698 A | 12/1990 | Stokley |
| 4,977,906 A | 12/1990 | DiScipio |
| 4,979,940 A | 12/1990 | Bobo, Jr. et al. |
| 4,981,467 A | 1/1991 | Bobo, Jr. et al. |
| 5,036,859 A | 8/1991 | Brown |
| 5,039,970 A | 8/1991 | Cox |
| 5,084,026 A | 1/1992 | Shapiro |
| 5,088,990 A | 2/1992 | Hivale et al. |
| 5,121,630 A | 6/1992 | Calvin |
| 5,137,033 A | 8/1992 | Norton |
| 5,139,482 A | 8/1992 | Simeon et al. |
| 5,197,958 A | 3/1993 | Howell |
| 5,247,434 A | 9/1993 | Peterson et al. |
| 5,264,830 A | 11/1993 | Kline et al. |
| 5,266,928 A | 11/1993 | Johnston |
| 5,291,181 A | 3/1994 | DePonte |
| 5,314,410 A | 5/1994 | Marks |
| 5,341,127 A | 8/1994 | Smith |
| 5,354,289 A | 10/1994 | Mitchell et al. |
| 5,389,093 A | 2/1995 | Howell |
| 5,392,032 A | 2/1995 | Kline et al. |
| 5,395,358 A | 3/1995 | Lu |
| 5,416,027 A | 5/1995 | Baudin et al. |
| 5,435,010 A | 7/1995 | May |
| 5,439,442 A | 8/1995 | Bellifemine |
| 5,468,236 A | 11/1995 | Everhart et al. |
| 5,469,145 A | 11/1995 | Johnson |
| 5,486,286 A | 1/1996 | Peterson et al. |
| 5,487,827 A | 1/1996 | Peterson et al. |
| 5,510,716 A | 4/1996 | Buffaloe, IV et al. |
| 5,510,717 A | 4/1996 | Buffaloe, IV et al. |
| 5,522,809 A | 6/1996 | Larsonneur |
| 5,542,932 A | 8/1996 | Daugherty |
| 5,557,263 A | 9/1996 | Fisher et al. |
| 5,568,128 A | 10/1996 | Nair |
| 5,570,026 A | 10/1996 | Buffaloe, IV et al. |
| 5,570,082 A | 10/1996 | Mahgereffeh et al. |
| 5,603,902 A | 2/1997 | Maltais et al. |
| 5,649,914 A | 7/1997 | Glaug et al. |
| 5,657,000 A | 8/1997 | Ellinghoe |
| 5,670,050 A | 9/1997 | Brose et al. |
| 5,674,390 A | 10/1997 | Matthews et al. |
| 5,681,298 A | 10/1997 | Brunner et al. |
| 5,685,989 A | 11/1997 | Krivitski et al. |
| 5,690,610 A | 11/1997 | Ito et al. |
| 5,690,624 A | 11/1997 | Sasaki et al. |
| 5,702,376 A | 12/1997 | Glaug et al. |
| 5,702,377 A | 12/1997 | Collier, IV et al. |
| 5,744,027 A | 4/1998 | Connell et al. |
| 5,760,694 A | 6/1998 | Nissim et al. |
| 5,762,805 A | 6/1998 | Truitt et al. |
| 5,766,212 A | 6/1998 | Jitoe et al. |
| 5,790,035 A | 8/1998 | Ho |
| 5,790,036 A | 8/1998 | Fisher et al. |
| 6,077,443 A | 6/2000 | Goldau |
| 6,572,576 B2 | 6/2003 | Brugger et al. |
| 6,663,585 B1 | 12/2003 | Ender |
| 6,932,786 B2 | 8/2005 | Giacomelli et al. |
| 7,052,480 B2 | 5/2006 | Han et al. |
| 7,138,088 B2 | 11/2006 | Wariar et al. |
| 2002/0198483 A1 | 12/2002 | Wariar et al. |
| 2003/0036719 A1 | 2/2003 | Giacomelli et al. |
| 2003/0128125 A1 | 7/2003 | Burbank et al. |
| 2003/0194894 A1 | 10/2003 | Wariar et al. |
| 2003/0195454 A1 | 10/2003 | Wariar et al. |
| 2004/0254513 A1 | 12/2004 | Shang et al. |
| 2005/0038325 A1 | 2/2005 | Moll |
| 2008/0065006 A1 | 3/2008 | Roger |
| 2008/0195021 A1 | 8/2008 | Roger |
| 2008/0195060 A1 | 8/2008 | Roger |
| 2009/0079578 A1 | 3/2009 | Dvorsky |
| 2009/0080757 A1 | 3/2009 | Roger |
| 2009/0082646 A1 | 3/2009 | Bouton |
| 2009/0082647 A1 | 3/2009 | Busby |
| 2009/0082649 A1 | 3/2009 | Muller |
| 2009/0082653 A1 | 3/2009 | Rohde |
| 2009/0082676 A1 | 3/2009 | Bennison |
| 2009/0088613 A1 | 4/2009 | Marttila |
| 2009/0088683 A1 | 4/2009 | Roger |
| 2009/0105627 A1 | 4/2009 | Rohde |
| 2010/0022934 A1 | 1/2010 | Hogard |
| 2010/0022935 A1 | 1/2010 | Muller |

FOREIGN PATENT DOCUMENTS

| | | |
|---|---|---|
| DE | 2838414 | 3/1980 |
| DE | 2948768 | 6/1981 |
| DE | 3045514 | 7/1982 |
| DE | 3223086 | 7/1983 |
| DE | 3440584 | 5/1986 |
| DE | 3823859 | 1/1990 |
| DE | 3836712 | 5/1990 |
| DE | 4000961 | 7/1991 |
| DE | 4014572 | 11/1991 |
| DE | 4018953 | 1/1992 |
| DE | 4023336 | 2/1992 |
| DE | 4239937 | 8/1995 |
| DE | 19823836 | 12/1999 |
| DE | 19901078 | 2/2000 |
| EP | 270048 | 6/1988 |
| EP | 328162 | 5/1989 |
| EP | 328163 | 5/1989 |
| EP | 332330 | 2/1990 |
| EP | 688531 | 12/1995 |
| EP | 551043 | 7/1996 |
| EP | 820776 | 1/1998 |
| EP | 835669 | 4/1998 |
| EP | 590810 | 7/1998 |
| EP | 895787 | 2/1999 |
| EP | 611228 | 4/1999 |
| EP | 911044 | 4/1999 |
| EP | 745400 | 12/1999 |
| FR | 2680678 | 3/1993 |
| FR | 2737124 | 1/1997 |
| GB | 2145859 | 4/1985 |
| GB | 2177247 | 6/1987 |
| GB | 2250121 | 5/1992 |
| JP | 4008361 | 1/1992 |
| JP | 6178789 | 6/1994 |
| JP | 10211278 | 8/1998 |
| JP | 11104233 | 4/1999 |
| JP | 11299889 | 11/1999 |
| JP | 20000140092 | 5/2000 |
| WO | WO 86/04710 | 8/1986 |
| WO | WO 94/02918 | 2/1994 |

| | | | | | | |
|---|---|---|---|---|---|---|
| WO | WO 94/07224 | 3/1994 | | WO | WO 99/26686 | 6/1999 |
| WO | WO 96/25904 | 8/1996 | | WO | WO 99/29356 | 6/1999 |
| WO | WO 97/10013 | 3/1997 | | WO | WO 99/42151 | 8/1999 |
| WO | WO 98/32476 | 7/1998 | | WO | WO 00/38761 | 7/2000 |
| WO | WO 99/12588 | 3/1999 | | WO | WO 01/06975 | 2/2001 |
| WO | WO 99/24145 | 5/1999 | | WO | WO 2006/044677 | 4/2006 |

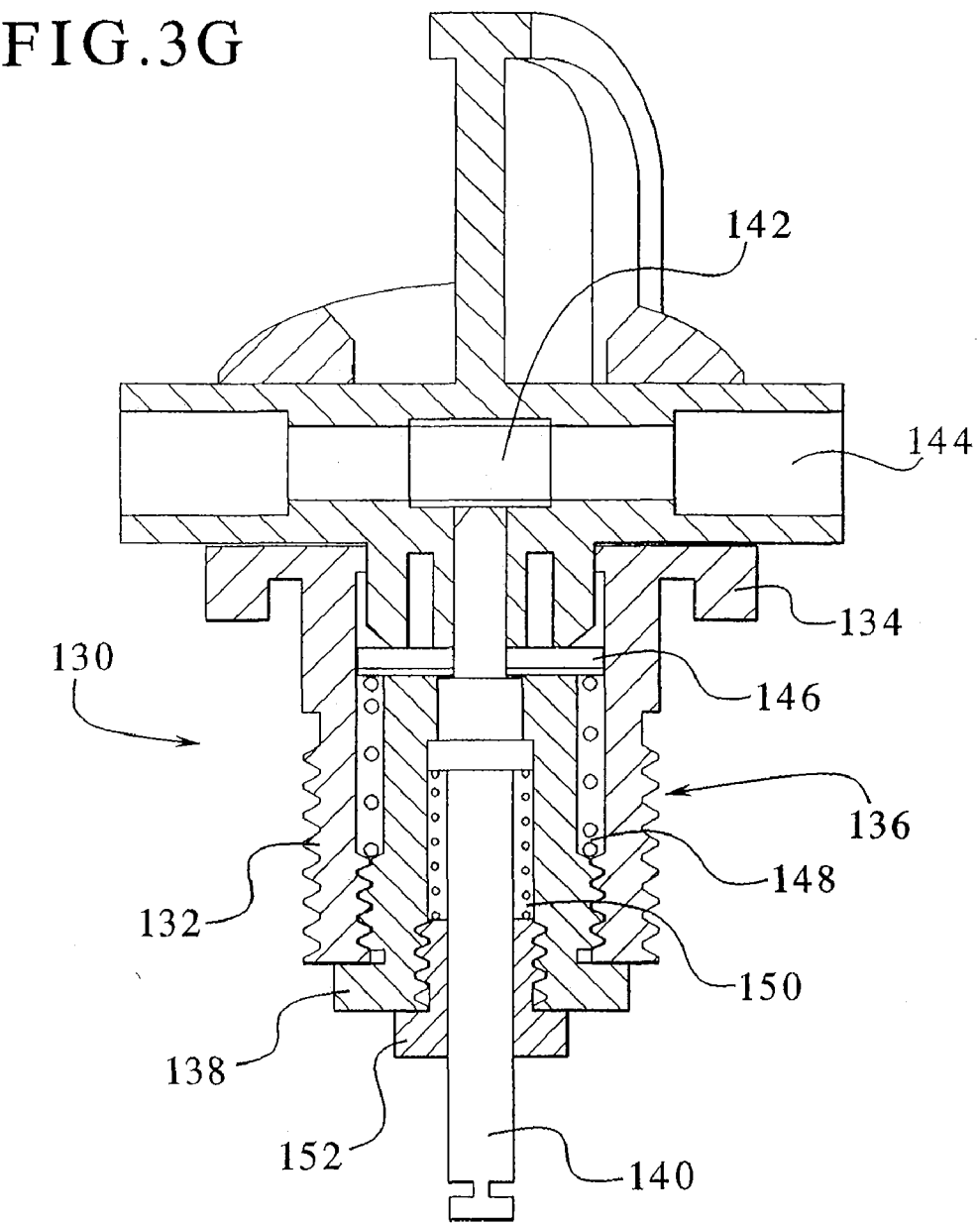

ACCESS DISCONNECTION SYSTEMS AND METHODS USING CONDUCTIVE CONTACTS

PRIORITY

This application is a continuation of U.S. patent application Ser. No. 11/331,609 filed Jan. 16, 2006, entitled "ACCESS DISCONNECTION SYSTEM AND METHODS", which is a continuation of U.S. patent application Ser. No. 10/120,684 filed Apr. 10, 2002, entitled "ACCESS DISCONNECTION SYSTEM AND METHODS" now U.S. Pat. No. 7,052,480, the entire contents of each of which are hereby incorporated by reference and relied upon.

BACKGROUND OF THE INVENTION

The present invention relates generally to patient access disconnection systems and methods for medical treatments. More specifically, the present invention relates to the detection of patient access disconnection, such as the detection of needle or catheter dislodgment during dialysis therapy.

A variety of different medical treatments relate to the delivery of fluid to, through and/or from a patient, such as the delivery of blood between a patient and an extracorporeal system connected to the patient via a needle or needles inserted within the patient. For example, hemodialysis, hemofiltration and hemodiafiltration are all treatments that remove waste, toxins and excess water directly from the patient's blood. During these treatments, the patient is connected to an extracoporeal machine, and the patient's blood is pumped through the machine. Waste, toxins and excess water are removed from the patient's blood, and the blood is infused back into the patient. Needles or similar access devices can be inserted into the patient's vascular access in order to transfer the patient's blood to and from the extracoporeal machine. Traditional hemodialysis, hemofiltration and hemodiafiltration treatments can last several hours and are generally performed in a treatment center about three to four times per week.

During any of these hemo treatments, dislodgment of an access device can occur, such as dislodgment of a needle or access device inserted into the patient's vascular access including an arterio-venous graft or fistula. If not detected immediately, this can produce a significant amount of blood loss to the patient. The risks associated with a needle dislodgment or other suitable condition are considerable. In this regard, important criteria for monitoring blood loss include, for example, the sensitivity, specificity and response time with respect to the detection of needle dislodgment. With increased levels of sensitivity, specificity, and response time, the detection of needle dislodgment can be enhanced, and blood loss due to dislodgment can be minimized.

Typically, patients undergoing medical treatment, such as hemodialysis, hemofiltration or hemodiafiltration, are visually monitored in order to detect needle dislodgment. However, the needle may not be in plain view of the patient or medical staff (i.e., it may be covered by a blanket) such that it could delay detection and, thus, responsive actions to be taken in view of dislodgment, such as stopping the blood pump of the extracorporeal machine to minimize blood loss to the patient.

Moreover, in view of the increased quality of life, observed reductions in both morbidity and mortality and lower costs than in-center treatments, a renewed interest has arisen for self care and home hemo therapies. Such home hemo therapies (whether hemodialysis, hemofiltration or hemodiafiltration) allow for both nocturnal as well as daily treatments. During these self care and home hemo sessions, especially during a nocturnal home hemo session, when the patient is asleep, dislodgment risks are more significant because nurses or other attendants are not present to detect the dislodgment.

Although devices that employ a variety of different sensors are available and known for detecting and/or monitoring a variety of different bodily fluids, these devices may not be suitably adapted to detect needle dislodgment. For example, known devices that employ sensors including pH, temperature and conductivity have been utilized to detect bedwetting and diaper wetness. Further, devices that employ pressure sensors and/or flow sensing devices are known and used during medical treatment, such as dialysis therapy, to monitor fluid flow including blood flow to and/or from the patient. However, these types of detection devices may not provide an adequate level of sensitivity and responsiveness if applied to detecting blood loss from the patient due to needle dislodgment. Although venous pressure is known to be used to monitor needle dislodgment, it is not very sensitive to needle-drop out.

Additional other devices and methods are generally known to monitor vascular access based on the electrical conductivity of blood. For example, Australian Patent No. 730,338 based on International Publication No. WO 99/12588 discloses an electronic device that induces a current in the extracorporeal blood circuit. The current is induced by a field coil placed around two points in the blood circuit thereby defining a closed conductor loop along the entire blood circuit. This can be problematic from both a patient health and safety perspective and the effective detection of needle-drop out or other vascular access conditions.

In this regard, the blood circuit is coupled to a blood treatment system that includes a number of high impedance components, such a blood pump, air bubble traps, pinch clamps and/or the like. Because of the large impedance of the conducting fluid-loop (due to the peristaltic pump and other components), the induction and detection of a patient-safe current requires an impractically complex design of the coil and system. Further, a high level of noise would necessarily result from the use of such levels of induced current. This can adversely impact the sensitivity of detection. If lower currents are used, the field coil would have to be increased in size to detect such low current levels. This may not be practical in use, particularly as applied during dialysis therapy.

PCT Publication No. WO 01/47581 discloses a method and device for monitoring access to the cardiovascular system of a patient. The access monitoring employs an electrical circuit which can generate and detect a current at separate points along a blood circuit connected to the patient. Electrical current is injected into the fluid using capacitive couplers that each have a metal tube placed around the blood circuit tubing. In this regard, the metal tube defines a first plate of a capacitor; the blood circuit tubing defines the dielectric; and the blood inside of the blood circuit tubing defines the second plate of the capacitor.

The generator applies a potential difference between a pair of capacitive couplers to generate a current in a segment of the blood circuit. A detector utilizes an additional and separate pair of capacitive couplers to measure the current along at least one section of the venous branch between a first contact point and the venous needle. The change in voltage (dV) can then be determined based on a measured change in current and compared to a reference range (I) to monitor access conditions. In this regard, PCT Publication No. WO 01/47581 requires a complex circuit design that utilizes multiple sets of capacitive couplers to maintain vascular access. This can increase the cost and expense of using same.

Further, the measure of capacitive coupling to inject and electric signal in the blood circuit and/or for detection purposes can be problematic. In this regard, the signal must pass through the tubing of the blood circuit as the tubing acts as a dielectric of the capacitor. This may cause an excess level of noise and/or other interference with respect to the detection of changes in vascular access conditions.

In this regard, it is believed that known devices, apparatuses and/or methods that can be used to monitor a patient's vascular access may not be capable of monitoring vascular access, particular the detection of needle-drop out during dialysis therapy, with sufficient sensitivity and specificity to ensure immediate detection of blood loss such that responsive measures can be taken to minimize blood loss. As applied, if twenty seconds or more of time elapses before blood loss due to dislodgment of the venous needle, over 100 milliliters in blood loss can occur at a blood flow rate of 400 ml/min, which is typical of dialysis therapy. Thus, the capability to respond quickly upon immediate detection of needle dislodgment is essential to ensure patient safety.

Accordingly, efforts have been directed at designing apparatuses, devices, systems and methods for detecting changes in access conditions, such as in response to needle dislodgment, wherein detection is sensitive, specific and immediate in response to such access changes such that responsive measures can be suitably taken to minimize blood loss from the patient due to same.

SUMMARY OF THE INVENTION

The present invention provides improved devices, apparatuses, systems and methods for detecting access disconnection during medical therapy. In particular, the present invention can detect dislodgment or disconnection of an access device, such as a needle, catheter or the like, inserted in a patient through which fluid can flow during medical therapy, such as dialysis therapy.

In general, the present invention includes any suitable type of electrical circuit that can generate, measure and/or process an electrical signal as it passes along a conductive path defined within a fluid circuit, such as an extracorporeal blood circuit during medical therapy including dialysis therapy. The blood circuit can be coupled to a blood treatment system through one or more access devices inserted within the patient. The access device can include, for example, needles, catheters or the like. In this regard, blood can be circulated into, through and out of the patient along the blood circuit.

The present invention can include a number of electrical connections and/or contacts that are spaced apart along the blood circuit to monitor patient access conditions. In particular, this can be used to detect access disconnection with high reliability. In this regard, the present invention can provide enhanced detection capabilities without requiring extensive modifications to the monitored therapy, such as to an extracorporeal blood circuit used during dialysis therapy. It is believed that the detection of access disconnection can also be achieved with the use of lower levels of current in contrast to known systems.

In an embodiment, the present invention includes a conductive connection or pathway along a fluid circuit, such as between an inflow fluid line and an outflow fluid line of the fluid circuit connecting a patient to a medical therapy system. This can define at least a segment including, for example, a loop along the fluid circuit, such as a extracorporeal blood circuit, that can remain closed until access disconnection. The loop can be adapted such that an electric current or other signal passing therein can bypass one or more components of a medical system coupled to the fluid circuit, such as dialysis system including a dialysis machine, a blood pump, a drip chamber, other like components and combinations thereof. The vascular access of the patient can then be monitored by measuring a change in an electrical value in response to access disconnection, such as dislodgment of a needle or catheter from the patient through which fluid can flow.

In an embodiment, the present invention can utilize at least three electrical contact points spaced apart and positioned along the blood circuit or other suitable fluid circuit to monitor access conditions. For example, an electrical signal, preferably a current, can be injected through a conductive pathway directly connecting a first contact point to a second contact point positioned along the blood circuit. As the electric signal passes therein, a change in an electrical value can then be measured using a third contact point positioned separate and apart from the first and second contact points. Alternatively, an electrical signal or the like can be injected into the fluid circuit through a single contact point where changes in the electrical value in response to dislodgment can then be measured using the direct connection between the two remaining electrical contact locations.

The present invention also provides an inductive coupler device that can be more easily and effectively utilized to attach an induction coil to a fluid circuit for detection purposes. In an embodiment, the inductive coupler includes movable members attached at an end region. A coil member, such as an induction coil, is placed around at least one of the movable members. This enables the induction coupler to move about the end region thus allowing it to be readily placed around and secured to a fluid conduit, such as a blood circuit. In this regard, the inductive coupler can be arranged in an open and closed position such that it can be readily secured to the fluid conduit. As used herein, the term "inductive coupler" or other like terms, such as "inductive coupling device" mean any suitable device which can be used to attach an induction coil to a fluid conduit, such as a blood circuit.

In an embodiment, the movable coupling members are composed of a material that has a high magnetic permeability. In this regard, the magnetic permeability of the movable coupling members is in an amount effective to converge or direct an electromagnetic field through the induction coil. This can enhance the electromagnetic flux through the induction coil such that an electromagnetic signal can be effectively injected and likewise measured in the blood circuit.

An advantage of the present invention is to provide improved apparatuses, devices, systems and/or methods for detecting access disconnection.

A further advantage of the present invention is to provide improved apparatuses, systems and/or methods for monitoring connections to a vascular access during dialysis therapy.

Another advantage of the present invention is to provide improved apparatuses, devices, systems and/or methods for access disconnection during selfcare and home hemo treatments, such as dislodgment of a needle, a catheter or the like.

Moreover, an advantage of the present invention is to provide improved apparatuses, devices, systems and/or methods for monitoring access disconnection with enhanced accuracy, sensitivity and responsiveness with respect to the detection of same.

Still further, an advantage of the present invention is to provide an improved device that can readily and effectively attach an induction coil to a fluid conduit used for detection purposes, such as detection of access disconnection.

Additional features and advantages of the present invention are described in, and will be apparent from, the following Detailed Description of the Invention and the figures.

BRIEF DESCRIPTION OF THE FIGURES

FIG. 3G illustrates a sectional view of FIG. 3F.

DETAILED DESCRIPTION OF THE INVENTION

Figure 1:
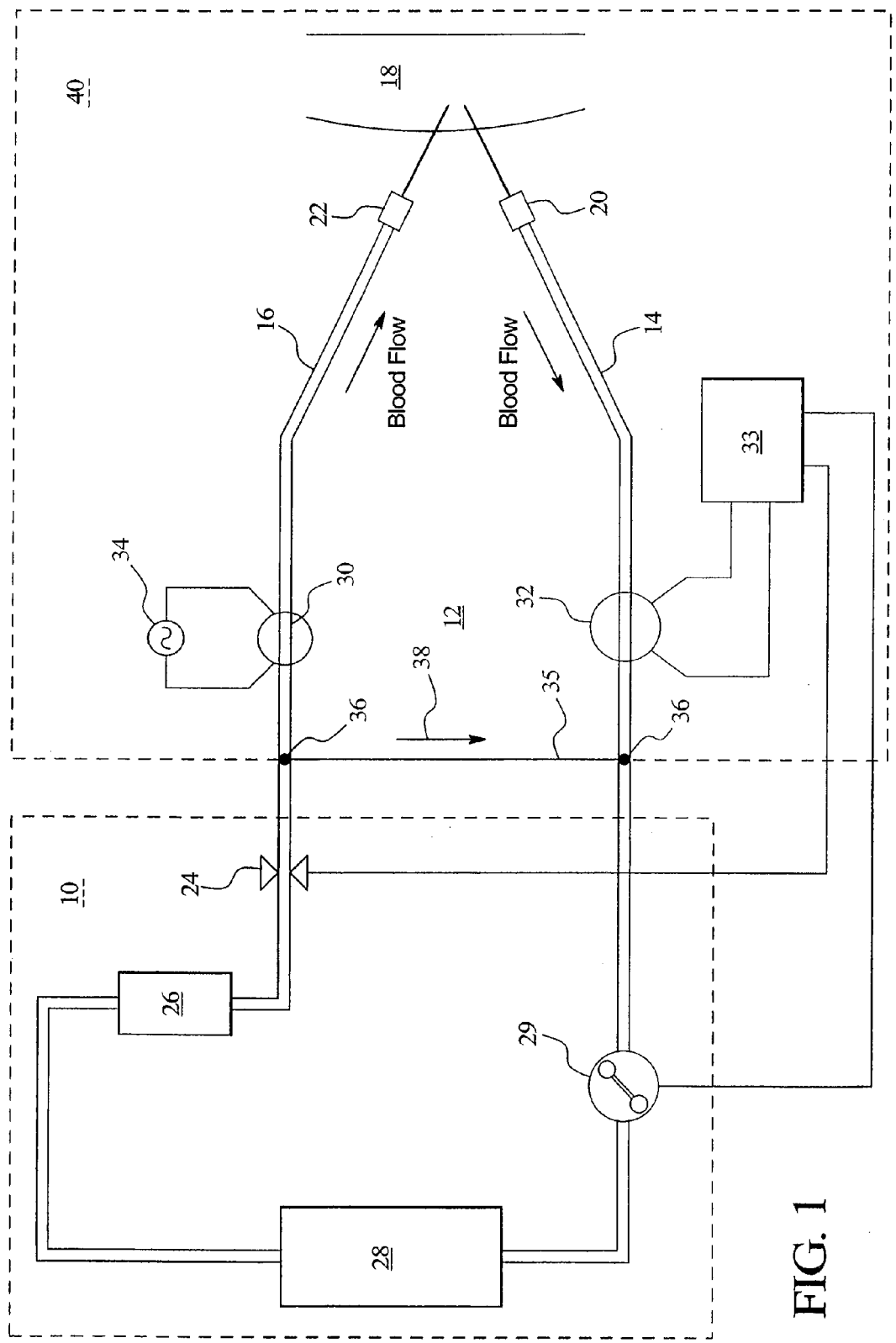
FIG. 1 illustrates an embodiment of the present invention showing a conductive connection that can be used to bypass one or more components of a blood treatment system coupled to a patient along a blood circuit.

The present invention relates to apparatuses, devices, systems, and/or methods for detecting access disconnection, such as dislodgment of a needle, catheter or other access device inserted in the vascular access of a patient undergoing medical therapy, such as dialysis therapy. In general, the present invention includes a suitable electrical circuit that provides any number and variety of suitable contact points spaced apart and coupled to a fluid circuit, such as a blood circuit. The contact points can be utilized to inject an electric signal into the fluid (e.g., blood) flowing through the fluid circuit thereby defining a conductor loop along at least a portion of the fluid circuit. A change in an electrical value in response to in response to changes in access conditions, such as access disconnection including needle-drop out.

It should be appreciated that the present invention is not limited to the detection of needle dislodgment but can be utilized to detect the dislodgment or disconnection of any suitable access device. As used herein, the term "access disconnection" or other like terms means any suitable condition or event which can cause a loss or leak of an electrically conductive fluid flowing along a fluid circuit connected to the patient provided that a change in the electrical continuity between electrical contacts coupled to the fluid circuit can be detected. It should be appreciated that a change in the electrical continuity as measured by an electrical value, such as impedance, may be detected even in the absence of dislodgment of an access device from the patient. The term "access device" as used herein or other like terms means a suitable device that can be inserted within a patient such that fluid, including blood, can pass to, through and/or from the patient via the access device. The access device can include a variety of different and suitable shapes, sizes and material make-up. Examples of an access device includes needles, catheters, cannulas or the like. The access device can be composed of any suitable material including, for example, stainless steel, plastic or like biocompatible materials.

Although in the embodiment set forth below the apparatus and/or device is designed for use in a dialysis therapy, such as hemodialysis, hemofiltration or hemodiafiltration, it should be noted that the present invention can be used in a number of different medical therapies that employ a variety of different and suitable fluid systems, such as extracorporeal blood systems. For example, the invention of the present application can be used during intravenous infusion that can employ the use of a single needle insertable within the patient for delivering a medical solution or drug, blood, blood products, processed blood or the like between the patient and the fluid system. In addition, the present invention can be used in plasma exchange therapies, where a membrane is used to separate whole blood into plasma and cellular components.

With respect to dialysis therapy, the present invention can be used in a variety of different therapies to treat kidney failure. Dialysis therapy as the term or like terms are used throughout the text is meant to include and encompass any and all forms of therapies that utilize the patient's blood to remove waste, toxins and excess water from the patient. Such therapies include both intermittent, including hemodialysis, hemofiltration and hemodiafiltration, and continuous therapies used for continuous renal replacement therapy (CRRT). These continuous therapies include slow continuous ultrafiltration (SCUF), continuous veno venous hemofiltration (CVVH), continuous veno venous hemodialysis (CVVHD), and continuous veno venous hemodiafiltration (CVVHDF). Dialysis therapy can also include peritoneal dialysis, such a continuous ambulatory peritoneal dialysis, automated peritoneal dialysis and continuous flow peritoneal dialysis. Further, although the present invention, in an embodiment, can be utilized in methods providing a dialysis therapy for patients having chronic kidney failure or disease, it should be appreciated that the present invention can be used for acute dialysis needs, for example, in an emergency room setting. Lastly, as one of skill in the art appreciates, the intermittent forms of therapy (i.e., hemofiltration, hemodialysis and hemodiafiltration) may be used in the in center, self/limited care as well as the home settings.

Access Disconnection

Figure 2A:
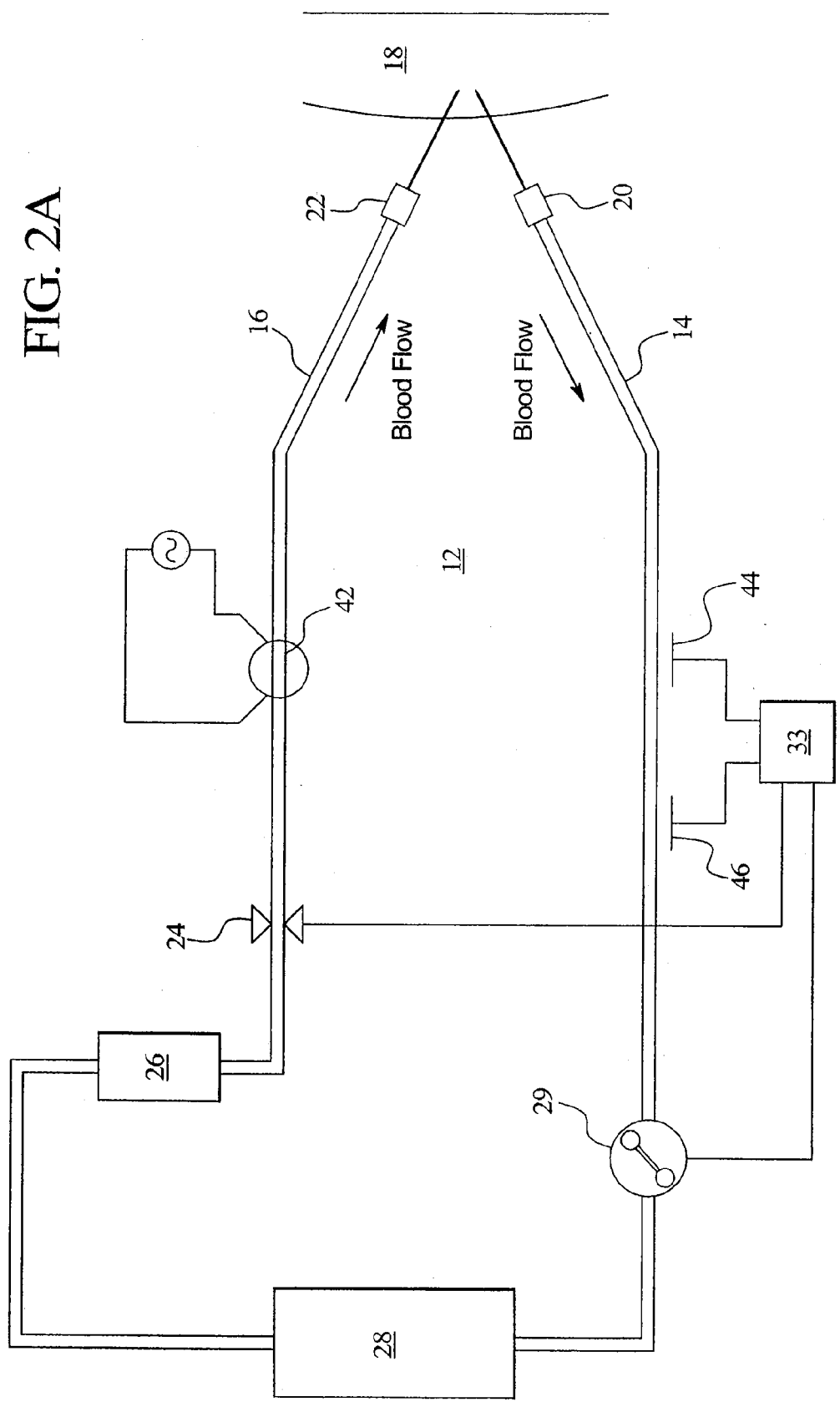
FIG. 2A illustrates injection of an electrical signal into the blood circuit using a conductive connection pursuant to an embodiment of the present invention.
Figure 2B:
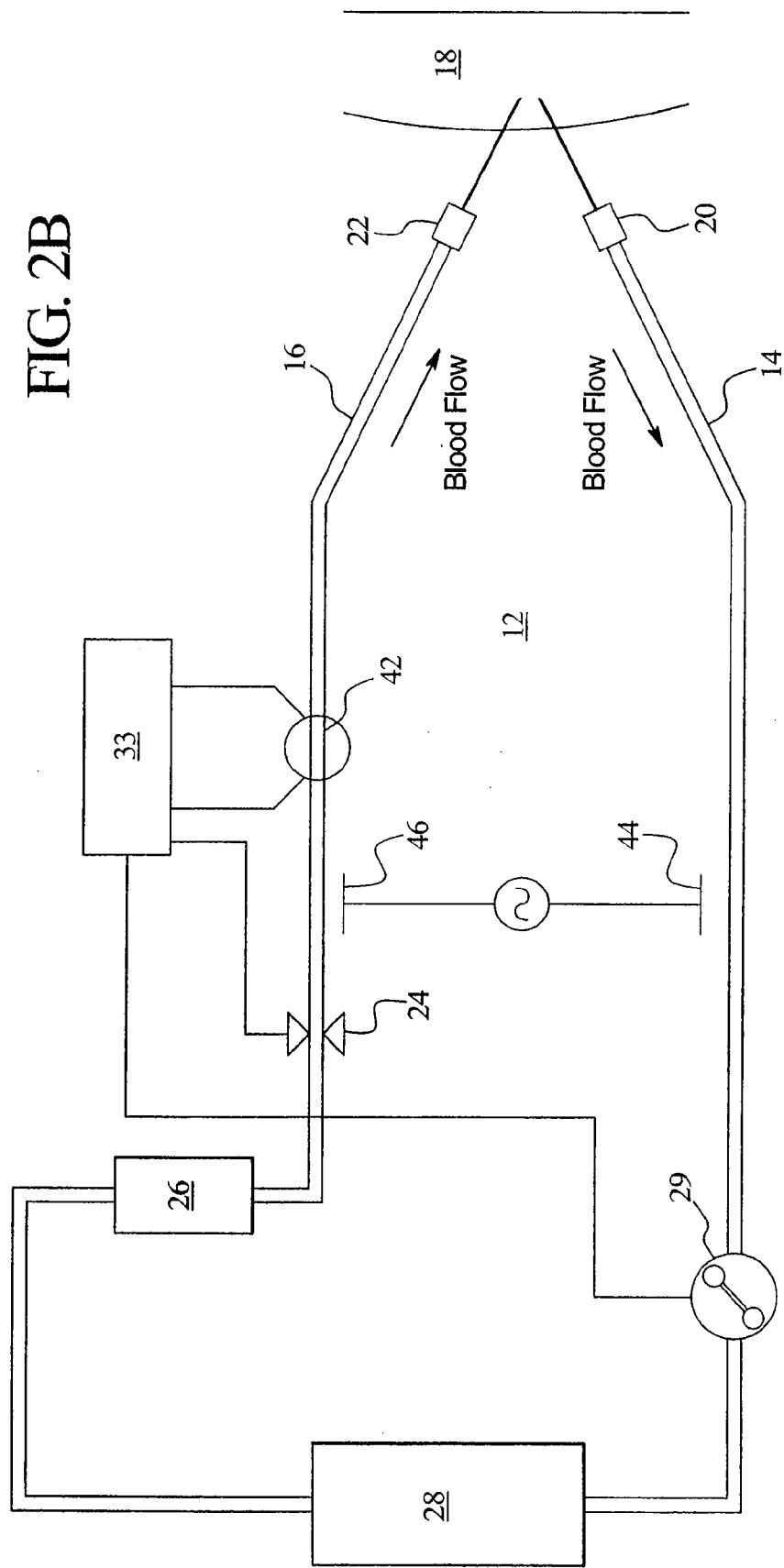
FIG. 2B illustrates measurement of a change in an electrical value in response to access disconnection using a conductive connection pursuant to an embodiment of the present invention.

As illustrated in FIGS. 1, 2A and 2B, the present invention, in an embodiment, can be adapted to monitor access conditions during dialysis therapy. A patient is connected to a dialysis system 10 via an extracorporeal blood circuit 12 that includes an arterial blood line 14 and a venous blood line 16 coupled to a vascular access 18 of the patient via an arterial needle 20 and a venous needle 22 or other suitable access device as shown in FIG. 1. In this regard, blood can circulate into, through and out of the patient along the blood circuit 12 during dialysis therapy.

The dialysis system 10 can include any number and variety of components. For example, the dialysis system includes any suitable clamp 24 or other flow regulator, an air bubble trap or the like 26, a blood treatment device 28, such as a dialyzer and a blood pump 29, such as a peristaltic pump. The components can be coupled to the blood circuit as schematically shown in FIG. 1. Any one or combination of these components can be apart of a dialysis machine coupled to the blood circuit, as described below. During treatment, blood passes from the patient through the arterial blood line 14, into the blood treatment device 28 and circulates back into the patient along the venous blood line 16.

As previously discussed, the present invention can include any suitable type of electrical circuit and design to effectively detect access disconnection during medical therapy. In an embodiment, the present invention includes a pair of induction coils attached to the blood circuit 12 at separate locations. As shown in FIG. 1, a first induction coil 30 is attached to the venous blood line 16 and a second induction coil 32 is attached to the arterial blood line 14.

It should be appreciated that any suitable type of induction coil can be utilized, such as a field coil coupled to and around the blood circuit. The induction coil can be attached to the fluid circuit in any suitable way. For example, the field coil can be wound around the fluid circuit. In an embodiment, the induction coil is placed around at least one member of a movable coupling device. The coupling device can be opened and closed allowing the induction coil to be readily and effectively placed around the fluid circuit as described below.

In an embodiment, any suitable electric signal can be injected into the blood circuit. A level of current is generated with any suitable device 34 and injected into the blood circuit at the first induction coil 30 attached to the venous blood line 16. As the electric current passes through the blood circuit 12, the second coil 32 can measure a change in an electrical value due to changes in access conditions during dialysis therapy. A change in amperage, impedance or the like can be detected with high reliability in response to dislodgment of one or both of the venous needle 22 and arterial needle 20 from the patient or other like devices. Alternatively, the electric current can be induced into the venous blood line and measured along the arterial blood line. As used herein, the term "electrical value" or other like terms means any suitable electrical parameter typically associated with electrical circuitry including, for example, impedance, resistance, voltage, current, rates of change thereof and combinations thereof.

The induction coil 32 can be used to pass a signal based on the measurable change in amperage or the like due to changes in access conditions, such as needle or drop-out. The signal can then be detected and further processed by a signal processing unit 33 connected to the induction coil 32. The signal processing unit 33 can then be coupled to any suitable component of the blood treatment system, such as the blood pump 29 and the clamp 24. In this regard, the blood pump 29 can be automatically shut off and/or the clamp 24 can be automatically closed to controllably minimize blood loss to the patient in response to, for example, needle-drop out or other suitable access disconnection conditions.

Conductive Bypass

As shown in FIG. 1, the present invention includes a conductive connection 35 made between two contact points 36 positioned along the arterial blood line 14 and venous blood line 16. This forms a conductive pathway 38 thereby defining a conductor loop 40 that remains closed until access disconnection. This allows the electric signal passing therein to bypass one or more of the components of the dialysis system along the blood circuit. In an embodiment, the conductive connection 35 can be positioned allowing the conductive pathway to bypass all of the components of the dialysis system 10 as shown in FIG. 1.

The bypass effectively acts to reduce the high impedance effects of various components of the dialysis system, such as the air bubble trap 26, the blood treatment device 28, the blood pump 29, the like and combinations thereof. In this regard, the injection of a high level of current or the like into the blood circuit is not required to overcome the high impedance effects of such components. This can facilitate the reliable detection of a change in impedance or other suitable electrical value in response to needle dislodgment. The use of high levels of current can necessarily result in a high level of noise which may impact detection sensitivity. Further, the ability to inject a lower level of an electrical signal, preferably current, in the blood circuit can better ensure the health and safety of the patient.

The conductive connection 35 can be formed in any suitable way. In an embodiment, the conductive connection 35 includes the conductive path 38 in fluid contact with blood flowing through the arterial blood line 14 and venous blood line 16 at the two contact points 36. The conductive path 38 can be composed of any suitable conductive material, such as a wire or other like conductive material such that the conductive path 38 has an impedance that is less than the impedance of the component or components of the dialysis system 10 that are bypassed. The impedance of the conductive path 38 is less than the impedance of the components in an amount effective to cause the electric current to bypass the components, and thus follow the path of least resistance. Alternatively, the conductive connection 35 can be coupled to the venous and arterial blood lines with capacitive couplers and thus does not make fluid contact with the blood.

Conductive Connection

As illustrated in FIGS. 2A and 2B, the present invention can include three contact points positioned along the blood circuit 12. In an embodiment, the first contact point 42 includes an induction coil capable of inducing an electric current or the like into the blood circuit. It should be appreciated that the electrical current or other suitable signal can be injected into the blood circuit in any suitable way including using an induction coil (as previously discussed), a capacitive coupler, an electrical contact in fluid communication with the blood and the like. The first contact point 42 is located on the venous blood line 16 at a position before the components of the dialysis system (refer to FIG. 1) along the blood circuit 12. The second contact point 44 is located on the arterial blood line 14 at a position before the components of the dialysis system along the blood circuit 12. Alternatively, the first 42 and second 44 contacts can be located on the arterial blood line 14 and the venous blood line 16, respectively.

The third contact point 46 can be located at any suitable position between the first 42 and second contact 44 points along a portion of the blood circuit 12 that connects the first 42 and second 44 contact points to the components of the dialysis system as shown in FIGS. 2A and 2B. The second 44 and third 46 contact points form a direct conductive connection in the blood circuit 12. The direct connection between the second 44 and third 46 contact points can be made in any suitable way. For example, the second contact 44 and the third contact 46 can be attached to the blood circuit 12 via an induction coil, an electrical contact in fluid contact with the blood, an electrical contact capacitively coupled to the blood circuit and/or the like as the fluid flows along the blood circuit 12. Any suitable device can be used to make an electrical connection with the fluid circuit, illustrative examples of which are described in detail below.

In an embodiment, the electric signal is injected into the blood circuit through the first contact point 42 in any suitable way, such as through an induction coil, thereby defining a conductor loop along the blood circuit. The conductive connection made directly between the second 44 and third 46 contact points can be utilized to measure a change in an electrical value in response to access disconnection as shown in FIG. 2A. Alternatively, the electrical signal can be generated and injected through the direct conductive connection where the first contact point 42 is used to measure a detectable change in the electrical value, such as impedance or the like as shown in FIG. 2B.

The use of the direct connection between the second 44 and third 46 contact points can facilitate the reliable detection of access disconnection, such as needle or catheter dislodgment. In this regard, a lower level of current or the like can be used to for detection purposes. From a practical standpoint, it is believed that the use of the direct connection can be achieved without requiring extensive modifications to the blood circuit as previously discussed.

The present invention provides a variety of different ways in which an electrical contact can be attached to a fluid circuit, such as a blood circuit, for use during detection of access detection. By way of example and not limitation, illustrative examples are described below.

Induction Coil Coupling Device

Figure 3A:
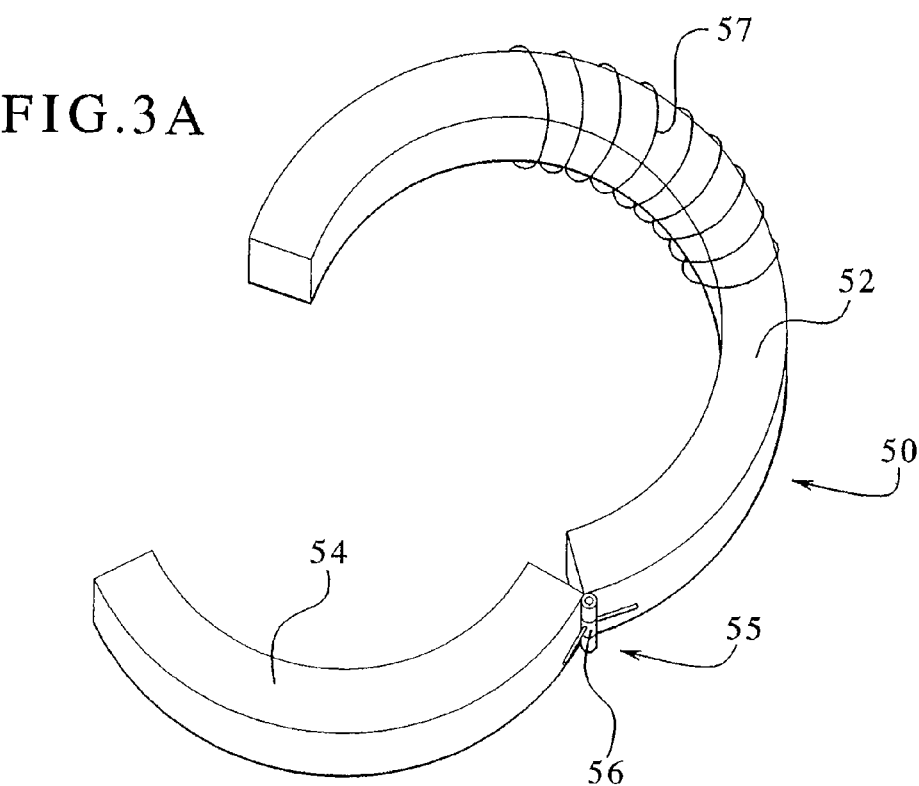
FIG. 3A illustrates an inductive coupler of an embodiment of the present invention in an open configuration as it is placed around a fluid conduit.
Figure 3B:
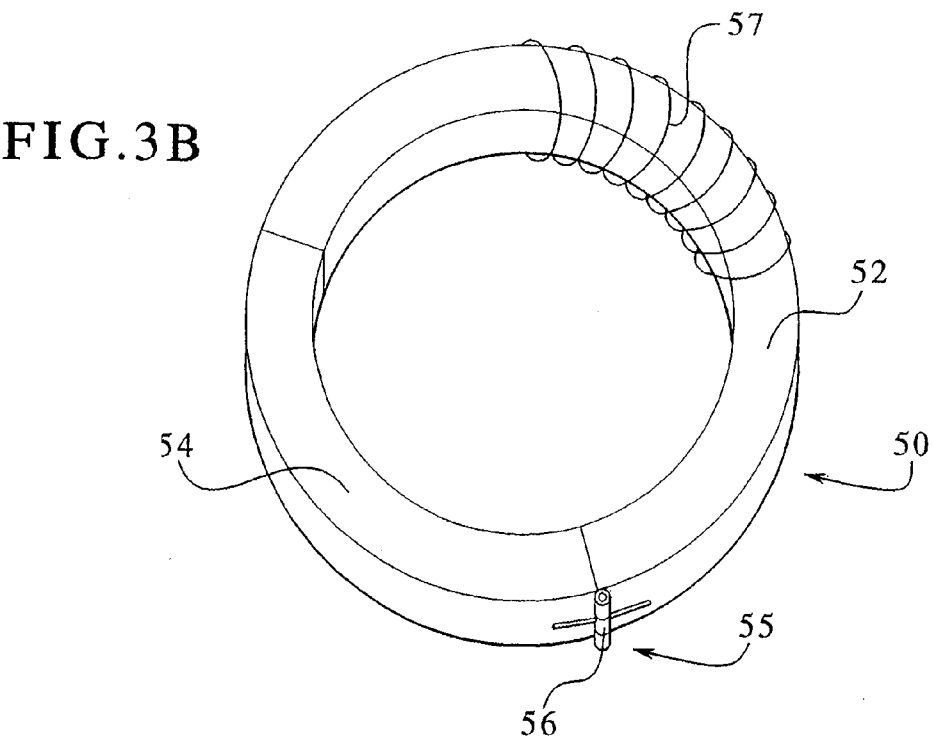
FIG. 3B illustrates an inductive coupler of an embodiment of the present invention in a closed configuration secured to the fluid conduit.

In an embodiment, the present invention includes an induction coil coupling device that can be more easily and effectively utilized to monitor vascular access during therapy. In an embodiment, the coupling device 50 of the present invention includes a first member 52 that is movably attached to a second member 54 at a first end 55 allowing displacement of the first member 52 and the second member 54 relative to one another. The first member 52 and the second member 54 can be movable attached in any suitable manner. For example, a hinge 56 or any other suitable movable device can be used. A coiled member 57, preferably an induction coil 57, is wrapped around at least a portion of the coupling device. In an embodiment, the induction coil is wrapped around a portion of the first movable member 52 as shown in FIGS. 3A and 3B. Alternatively the induction coil 57 can be wrapped around the second movable member 54, both members and portions thereof.

In FIG. 3A, the induction coupling device 50 of the present invention is in an open configuration such that it can be readily placed around a fluid conduit (not shown), such as a blood line of a blood circuit. Next, the first member 52 and/or the second member 54 can be displaced to close and secure the coupling device 50 to the blood line as shown in FIG. 3B. In an embodiment, the first member 52 and the second member 54 can be displaced to matingly engage in any suitable way at a second end. This enables the induction coupling device 50 to be easily attached to a blood circuit as compared to the mere use of an induction field coil which must necessarily be wound around the blood line of the blood circuit a multiple number of times for effective use.

In an embodiment, the movable members are composed of a material that has a high magnetic permeability, such as a ferrite bead. In the closed position, the movable members must meet in mating engagement. In this regard, the movable members can effect act to converge or direct an electromagnetic field through the induction coil 57. This can enhance the electromagnetic flux through the induction coil allowing the induction coupling device to be effectively used to detect access disconnection as previously discussed.

Electrical and Fluid Contact

In an embodiment, the present invention can include an electrical contact coupling device that can be utilized to secure the electrical contacts, preferably electrodes, to the blood circuit such that the electrodes effectively contact the blood and, thus, can be used to effectively monitor changes in access conditions as previously discussed. The coupling device of the present invention can also be designed to facilitate the protection of the user against contact with potential electrical sources. In an embodiment, the device can include a conductive element connected to a tube through which a medical fluid can flow wherein the conductive element has a first portion exposed to the medical fluid, such as blood, and a second portion external to the tube.

It should be appreciated that the coupling device of the present invention can include a variety of different and suitable configurations, components, material make-up or the like. In an embodiment, the present invention can include a device for connecting an electrical contact to a fluid conduit providing fluid and electrical communication between the electrical contact and fluid flowing through the fluid conduit. The device can include a first member including an, annular portion capable of accommodating the electrical contact and a first stem portion connected to the annular member wherein the stem portion has an opening extending therethrough to the annular portion; a second member including a base portion with a groove region and a second stem portion with an opening extending therethrough to the groove region allowing the first member to be inserted and secured to the second member; and a contact member adapted to fit the first and second stem portions allowing the contact member to abut against at least a portion of the electrical contact member allowing an electrical connection to be made between the electrical contact and the contact member.

Figure 3C:
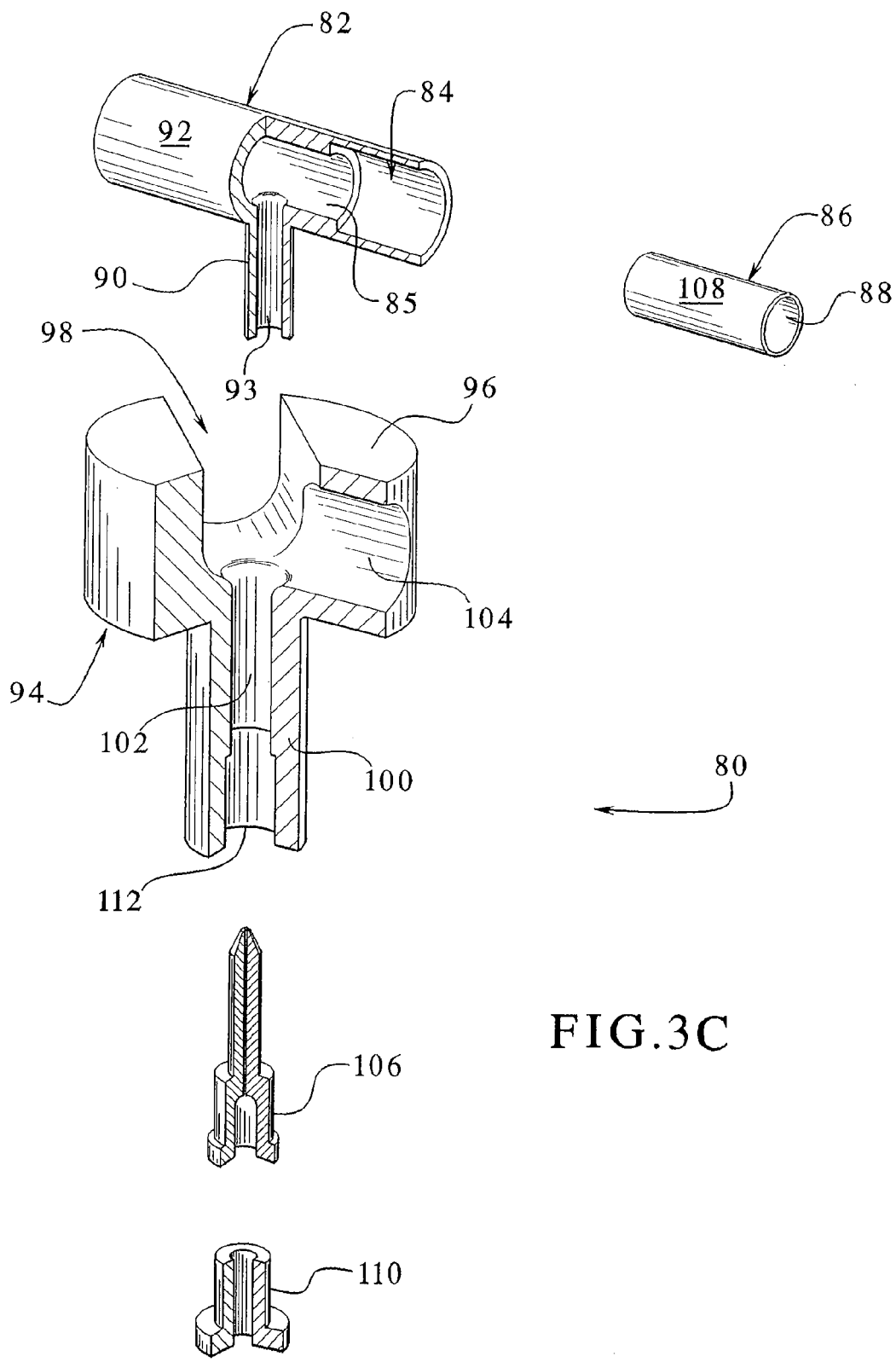
FIG. 3C illustrates an exploded view of an electrical contact, coupling device in an embodiment of the present invention.
Figure 3D:
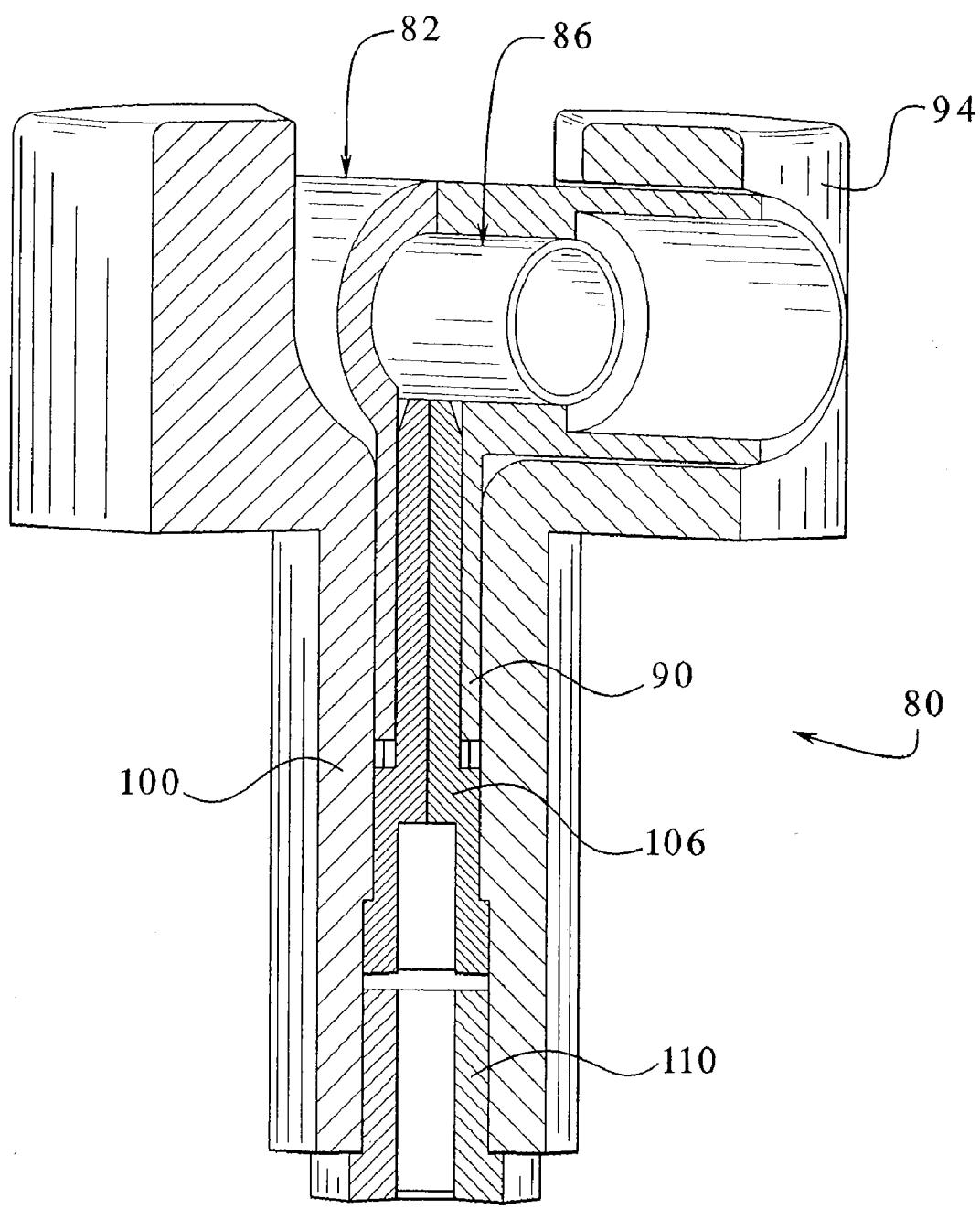
FIG. 3D illustrates a side sectional view of the coupling device of FIG. 3C in an embodiment of the present invention.

As illustrated in FIGS. 3C and 3D, the electrical contact coupling device 80 includes a probe member 82 that has a cylindrical shape with an opening 84 extending therethrough. In this regard, an electrical contact, preferably an electrode 86 having a cylindrical shape can be inserted into the opening 84 such that the electrode 86 is secure within the probe member 82. In an embodiment, the probe member 82 has a channel 85 extending along at least a portion of the opening 84 within which the electrode 86 can be inserted into the probe member 82. A tube member, for example, from a blood tubing set, connector tube member of a dialysis machine or the like, can be inserted into both ends of the opening 84 of the probe member 82 in contact with an outer portion of the channel 85 allowing blood or other suitable fluid to make fluid contact with the electrode 86 in any suitable manner. The electrode 86 has an opening 88 that extends therethrough within which blood (not shown) or other suitable fluid from the fluid circuit can flow. In an embodiment, the diameter of the opening 88 of the electrode 86 is sized to allow blood flow through the electrode 86 such that blood flow levels under typical operating conditions, such as during dialysis therapy, can be suitably maintained. In this regard, the coupling device of the present invention can be readily and effectively attached to a fluid circuit, including a blood circuit or the like, for use during medical therapy including, for example, dialysis therapy. It should be appreciated that the coupling device 80 of the present invention can be attached to the fluid circuit in any suitable way such that electrical and fluid connection can be made with the fluid flowing through the fluid circuit.

The probe member 82 also includes a stem portion 90 that extends from a surface 92 of its cylindrical-shaped body. The stem portion 90 has an opening 93 that extends therethrough. In an embodiment, the stem portion 90 is positioned such that at least a portion of the electrode 86 is in contact with the opening 93 of the stem portion 90.

In order to secure the electrode 86 to the blood circuit, the coupling device 80 includes a socket member 94 that includes a body portion 96 with an opening 98 for accepting the probe member 82 and for accepting a blood tube member (not shown) of the blood circuit such that blood directly contacts the electrode as it circulates through the blood circuit during dialysis therapy. In an embodiment, the socket member 94 includes a stem portion 100 extending from the body member 96 wherein the stem portion 100 includes an opening 102 extending therethrough. As the probe member 82 is inserted through the opening 98 of the body member 96, the stem portion 90 of the probe member 82 can be inserted into the opening 102 of the stem portion 100 of the body 96 of the socket member 94.

In an embodiment, the socket member 94 includes a groove region 104 extending along at least a portion of the body 96 of the socket member 94. In this regard, the probe member 82 can be inserted through the opening 98 and then moved or positioned into the groove region 104 to secure the probe member 82 within the body 96 of the socket member 94.

In an embodiment, the coupling device 80 includes an electrical contact member 106 that is inserted within the opening 102 of the stem portion 100 of the body 96 of the socket member 94 such that the electrical contact member 106 extends through the opening 93 of the stem portion 90 of the probe member 82 to contact at least a portion of a surface 108 of the electrode 86.

The electrical contact member 106 is utilized to connect the electronics (not shown) of, for example, the excitation source, a signal processing device, other like electronic devices suitable for use in monitoring and/or controlling changes in access conditions, such as needle dislodgment. The electrical contact member 106 can be made of any suitable material, such as any suitable conductive material including, stainless steel, other like conductive materials or combinations thereof. In order to secure the electrical contact member 106 in place, a contact retainer member 110 is inserted within the opening 102 of the stem portion 100 at an end region 112 thereof.

In an embodiment, the coupling device can be mounted to a dialysis machine, device or system in any suitable manner. For example, the coupling device can be mounted as an integral component of the dialysis machine. As well, the coupling device can be mounted as a separate and/or stand alone component which can interface with any of the components of the apparatus and system of the present invention. In an embodiment, the coupling device 80 can be insertably mounted via the stem portion 100 of the socket member 94 to a dialysis machine or other suitable components.

Figure 3E:
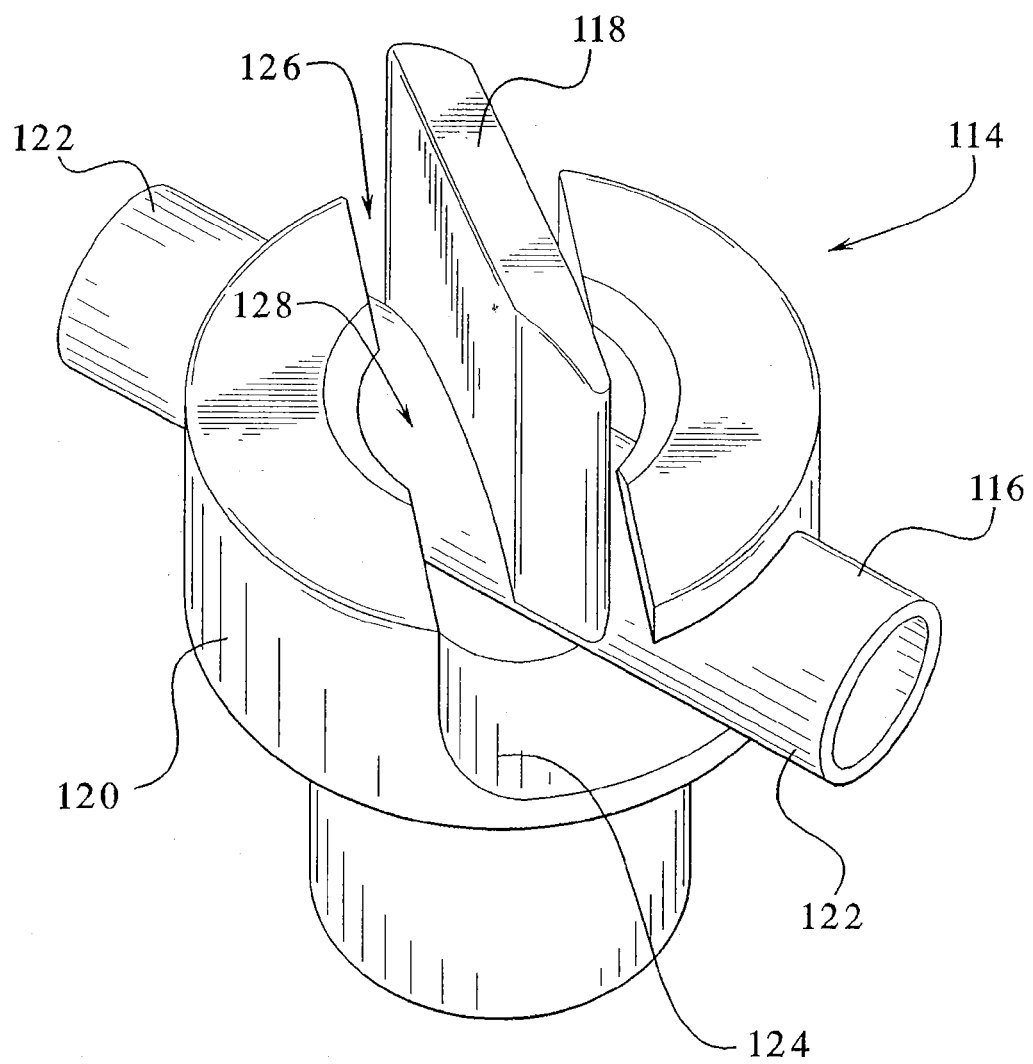
FIG. 3E illustrates another embodiment of the coupling device of the present invention.

It should be appreciated that the electrical contact coupling device can include a variety of different and suitable shapes, sizes and material components. For example, another embodiment of the coupling device is illustrated in FIG. 3E. The coupling device 114 in FIG. 3E is similar in construction to the coupling device as shown in FIGS. 3C and 3D. In this regard, the coupling device 114 of FIG. 3E can include, for example, a cylindrical-shaped electrode or other suitable electrical contact, a probe member for accepting the electrode and securing it in place within a socket member of the sensing device. The probe member includes a stem portion that is insertable within a stem portion of the socket member. An electrical contact member is insertable within the stem portion such that it can contact the electrode. The coupling device of FIG. 3E can also include a contact retainer member to hold the electrical contact member in place similar to the coupling device as shown in FIGS. 3C and 3D.

As shown in FIG. 3E, the probe member 116 of the electrical contact coupling device 114 includes a handle 118 which can facilitate securing the probe member 116 within the socket member 120. The handle 118, as shown, has a solid shape which can facilitate the use and manufacture of the coupling device 114. In addition, the stem portion (not shown) of the probe member 116 is larger in diameter than the stem portion of the probe member as illustrated in FIG. 3C. By increasing the stem size, the probe member can be more easily and readily inserted within the socket member. Further, the probe member is greater in length as compared to the probe member as shown in FIGS. 3C and 3D such that the end regions 122 of the probe member 116 extend beyond a groove region 124 of the socket member 120. This can facilitate securing the probe member within the groove region 124 of the socket member 120.

In an embodiment, an opening 126 of the socket member 120 can include an additional opening portion 128 to accommodate the insertion of the stem portion of the probe member 116, having an increased size, therethrough. This can ensure proper alignment of the probe member with respect to the socket member before insertion of the probe member into the socket member thus facilitating the insertion process.

It should be appreciated that the probe member, socket member and contact retainer member can be composed of a variety of different and suitable materials including, for example, plastics, molded plastics, like materials or combinations thereof. The various components of the coupling device, such as the probe member, socket member and contact retainer member, can be fitted in any suitable way. For example, the components can be fitted in smooth engagement (as shown in FIGS. 3C and 3D), in threaded engagement (as shown in FIGS. 3F and 3G) and/or any suitable fitting engagement or arrangement relative to one another.

Figure 3F:
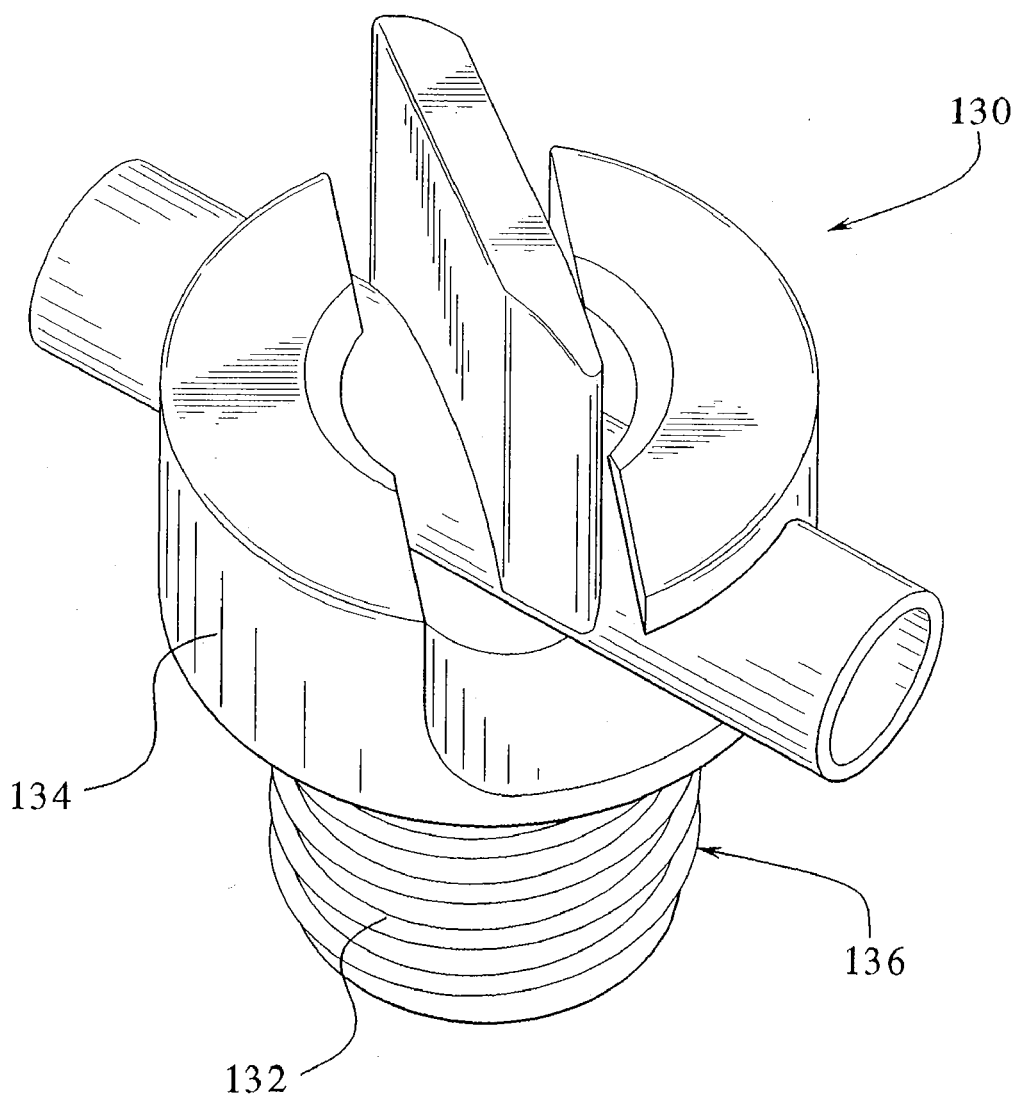
FIG. 3F illustrates another embodiment of the coupling device of the present invention showing a threaded engagement between the components of same.

As shown in FIGS. 3F and 3G, the coupling device 130 of the present invention can be made of threaded parts which are removably and insertably connected to one another to form the coupling device. The threaded parts can facilitate securing the electrode to the blood circuit as well as general use of same as described below.

In an embodiment, the stem portion 132 of the body 134 of the coupling device 130 has a threaded region 136 which can be insertably attached to a dialysis machine or other suitable mounting device in threaded engagement. This can facilitate the ease in which the coupling device is attached and detached from the mounting device.

As shown in FIG. 3G, the stem portion 132 is threaded on both sides allowing it to be in threaded engagement with an annular member 138. The annular member 138 provides direction and support allowing the electrical contact member 140 to abut against the electrode 142 housed in the probe member 144 as previously discussed.

In an embodiment, a plate member 146 made of any suitable conductive material can be depressed against a spring 148 as the probe member 144 is secured to the body 134. At the same time, another spring 150 can be displaced against the electrical contact member 140 in contact with the retainer 152 which is inserted within an annular region of the annular member 138 to secure the electrical contact member 140 to the body 134.

The spring mechanism in an embodiment of the present invention allows the parts of the coupling device 130 to remain in secure engagement during use. It can also facilitate use during detachment of the parts for cleaning, maintenance or other suitable purpose.

As previously discussed, the present invention can be effectively utilized to detect dislodgment of an access device, such as a needle or catheter, inserted within a patient through which fluid can pass between the patient and a fluid delivery and/or treatment system. The present invention can be applied in a number of different applications, such as medical therapies or treatments, particularly dialysis therapies. In dialysis therapies, access devices, such as needles or catheters, can be inserted into a patient's arteries and veins to connect blood flow to and from the dialysis machine.

Under these circumstances, if the access device becomes dislodged or separated from the blood circuit, particularly the venous needle, the amount of blood loss from the patient can be significant and immediate. In this regard, the present invention can be utilized to controllably and effectively minimize blood loss from a patient due to dislodgment of the access device, such as during dialysis therapy including hemodialysis, hemofiltration, hemodiafiltration and continuous renal replacement.

Dialysis Machine

As previously discussed, the present invention can be adapted for use with any suitable fluid delivery system, treatment system or the like. In an embodiment, the present invention is adapted for use with a dialysis machine to detect access disconnection as blood flows between the patient and the dialysis machine along a blood circuit during treatment, including, for example hemodialysis, hemofiltration and hemodiafiltration.

Figure 4A:
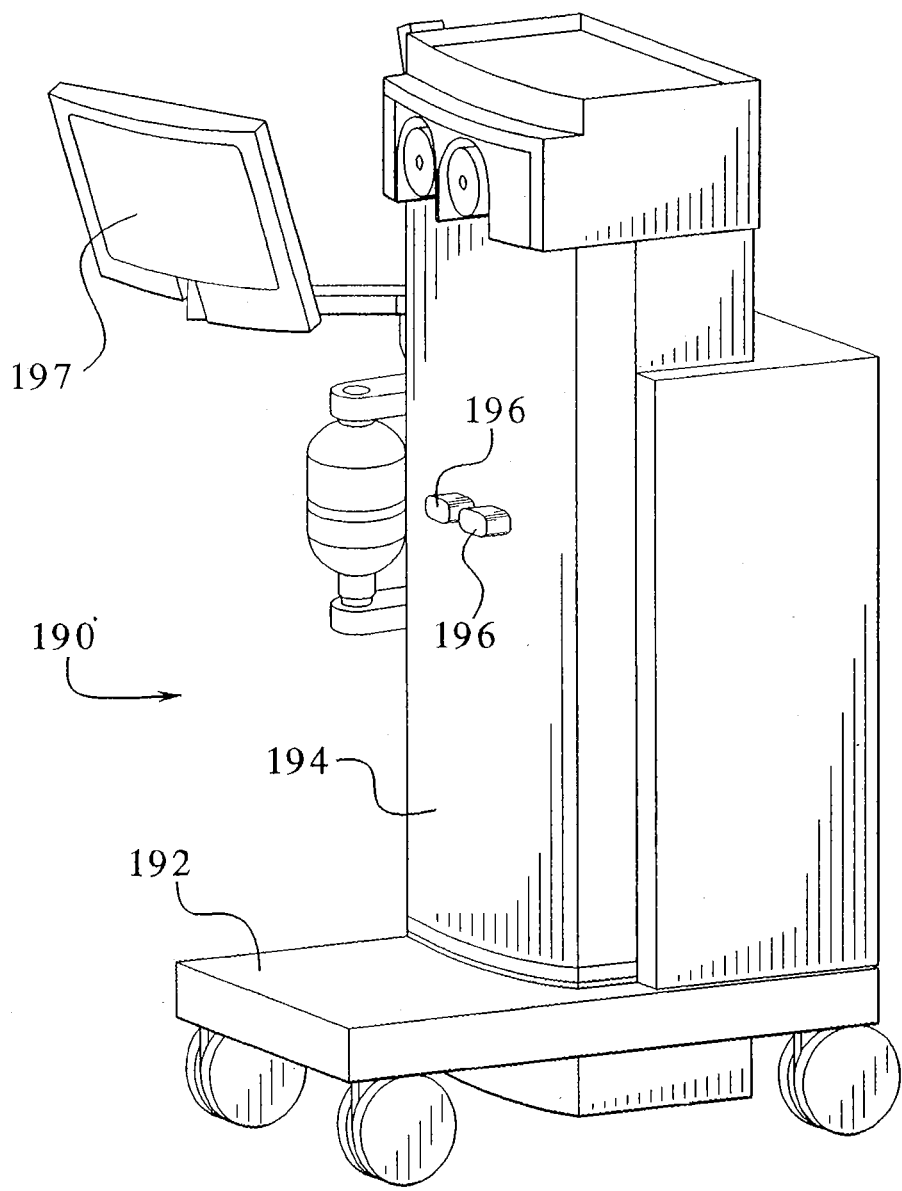
FIG. 4A illustrates a dialysis machine in an embodiment of the present invention.
Figure 4B:
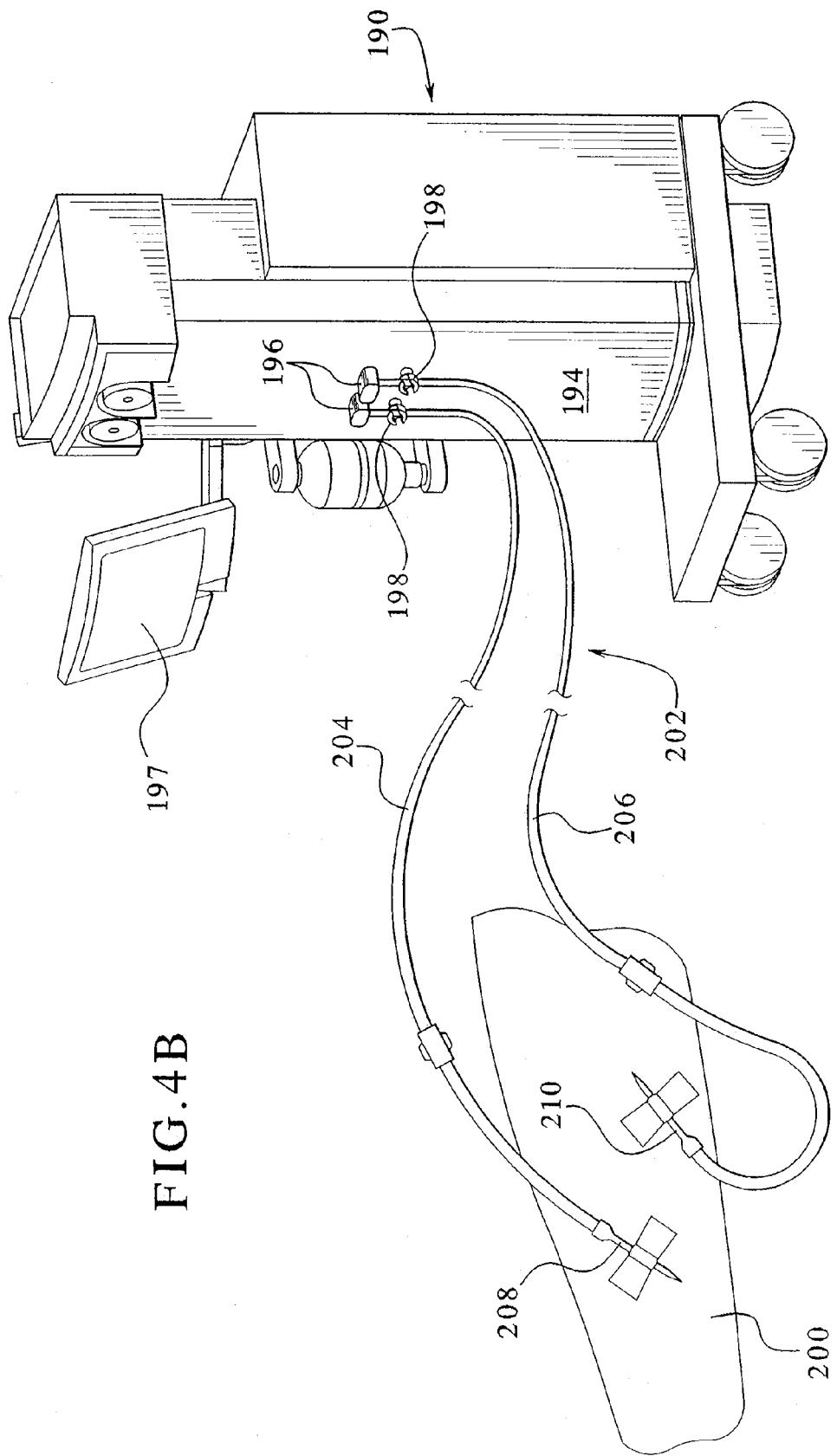
FIG. 4B illustrates a dialysis machine in another embodiment of the present invention.

The present invention can include any suitable dialysis machine for such purposes. An example, of a hemodialysis machine of the present invention is disclosed in U.S. Pat. No. 6,143,181 herein incorporated by reference. In an embodiment, the dialysis machine 190 comprises a mobile chassis 192 and it has at the front side 194 thereof a common mechanism 196 for connecting tubing or the like by which a patient can be connected to the dialysis machine as shown in FIG. 4B. A flat touch screen 197 which can show several operational parameters and is provided with symbols and fields for adjustment of the dialysis machine by relevant symbols and fields, respectively, on the screen being touched can be adjusted vertically and can be universally pivoted on the dialysis machine and can be fixed in the desired adjusted position.

In an embodiment, the dialysis machine includes a chassis having one or more connectors for connecting a patient to the dialysis machine via a blood circuit allowing blood to flow between the patient and the dialysis machine during dialysis therapy wherein one or more electrical contacts are connected to the blood circuit in fluid communication with the blood allowing detection of a change in an electrical value in response to access disconnection as the blood flows through the blood circuit having an electrical signal passing therein as previously discussed.

In an embodiment, the dialysis machine of the present invention can be designed to accommodate one or more of the coupling devices, such as an induction coil coupling device and other such coupling devices as previously discussed, used to detect access disconnection as shown in FIG. 4B. For example, one or more coupling devices 198 can be attached to the front panel 194 of the dialysis machine 190. This can be done in any suitable way. In an embodiment, a stem portion of the coupling device is insertably mounted via a threaded fit, frictional fit or the like, as previously discussed. This connects the patient to the dialysis machine 190 via a blood tubing set 202. The blood tubing set includes a first blood line 204 and a second blood line 206. In an embodiment, the first blood line 204 is connected to the patient via an arterial needle 208 or the like through which blood can flow from the patient 200 to the dialysis machine 190. The second blood line 206 is then connected to the patient 200 via a venous needle 210 or the like through which fluid flows from the dialysis machine to the patient thereby defining a blood circuit. Alternatively, the first blood line and the second blood line can be coupled to the venous needle and the arterial needle, respectively. The blood lines are made from any suitable medical grade material. In this regard, access disconnection, such as dislodgment of an arterial needle and/or a venous needle can be detected as previously discussed. Alternatively, the coupling device can be attached to the blood tubing set which is then attached to the dialysis machine in any suitable way.

Dialysis Treatment Centers

As previously discussed, the present invention can be used during dialysis therapy conducted at home and in dialysis treatment centers. The dialysis treatment centers can provide dialysis therapy to a number of patients. In this regard, the treatment centers include a number of dialysis machines to accommodate patient demands. The therapy sessions at dialysis treatment centers can be performed 24 hours a day, seven days a week depending on the locale and the patient demand for use.

In an embodiment, the dialysis treatment centers are provided with the capability to detect access disconnection during dialysis therapy pursuant to an embodiment of the present invention. For example, one or more of the dialysis machines within the center can be adapted for use with an electrical contact coupling, induction coil coupling device and/or the like along with other components necessary to detect access disconnection as previously discussed.

In an embodiment, the coupling device can be directly attached to one or more of the dialysis machines of the dialysis treatment center. It should be appreciated that the apparatuses, devices, methods and/or systems pursuant to an embodiment of the present invention can be applied for use during dialysis therapy administered to one or more patients in the dialysis treatment center in any suitable way. In an embodiment, the treatment center can have one or more patient stations at which dialysis therapy can be performed on one or more patients each coupled to a respective dialysis machine. Any suitable in-center therapy can be performed including, for example, hemodialysis, hemofiltration, hemodiafiltration, continuous renal replacement and combinations thereof. As used herein, the term "patient station" or other like terms mean any suitably defined area of the dialysis treatment center dedicated for use during dialysis therapy. The patient station can include any number and type of suitable equipment necessary to administer dialysis therapy.

In an embodiment, the dialysis treatment center includes a number of patient stations each at which dialysis therapy can be administered to one or more patients; and one or more dialysis machines located at a respective patient station. One or more of the dialysis machines can include a chassis having one or more connectors for connecting a patient to the dialysis machine via a blood circuit allowing blood to flow between the patient and the dialysis machine during dialysis therapy wherein a number of electrical contacts can be connected to the blood circuit in fluid communication with the blood allowing detection of a change in an electrical value in response to access disconnection as the blood flows through the blood circuit having an electrical signal passing therein.

As previously discussed, the access disconnection detection capabilities of the present invention can be utilized to monitor and control a safe and effective dialysis therapy. Upon dislodgment of an access device, such as a needle or catheter, from the patient, the access disconnection detection capabilities of the present invention can be used to provide a signal indicative of dislodgment that can be further processed for control and/or monitoring purposes. In an embodiment, the signal can be further processed to automatically terminate dialysis therapy to minimize blood loss due to dislodgment as previously discussed. Further, the signal can be processed to activate an alarm which can alert the patient and/or medical personnel to the dislodgment condition to ensure that responsive measures are taken. It should be appreciated that the present invention can be modified in a variety of suitable ways to facilitate the safe and effective administration of medical therapy, including dialysis therapy.

It should be understood that various changes and modifications to the presently preferred embodiments described herein will be apparent to those skilled in the art. Such changes and modifications can be made without departing from the spirit and scope of the present invention and without diminishing its intended advantages. It is therefore intended that such changes and modifications be covered by the appended claims.

The invention claimed is:

1. An extracorporeal blood system comprising:
an extracorporeal blood machine including an extracorporeal blood circuit;
an access device enabling the extracorporeal blood circuit to be connected to a patient;
first and second coupling devices for connecting respectively to first and second tubes of the extracorporeal circuit;
first and second electrodes held, at least in part, by the first and second coupling devices so as to contact blood flowing through the extracorporeal blood circuit, the first and second electrodes enabling an electrical signal to be injected into the extracorporeal blood circuit;
first and second contact members contacting the first and second electrodes respectively, wherein at least one of the first and second coupling devices includes a stem portion into which at least one of the first and second contact members is inserted to contact at least one of the first and second electrodes, respectively; and
electronics coupled operably to the first and second contact members for applying the electrical signal, the signal used to monitor the access device.

2. The extracorporeal blood system of claim 1, wherein the first and second electrodes are located within the first and second coupling devices, respectively.

3. The extracorporeal blood system of claim 1, wherein at least one of the first and second electrodes is located approximately at the middle of the at least one of the first and second coupling devices, respectively.

4. The extracorporeal blood system of claim 1, wherein at least one of the first and second coupling devices is configured to fit between two sections of tubing.

5. The extracorporeal blood system of claim 1, wherein the first and second contact members extend into the first and second coupling devices respectively.

6. The extracorporeal blood system of claim 1, wherein the access device includes first and second needles connected to the extracorporeal circuit.

7. The extracorporeal blood system of claim 1, wherein the first and second tubes are arterial and venous lines, respectively.

8. The extracorporeal blood system of claim 7, wherein the first coupling device, connected to the arterial line, is located upstream of a blood pump operational area of the arterial line.

9. The extracorporeal blood system of claim 7, wherein the second coupling device, connected to the venous line, is located downstream of an air trap located in the arterial line.

10. The extracorporeal blood system of claim 1, wherein the electronics includes a current generation source.

11. An extracorporeal blood system comprising:
an extracorporeal blood machine including an extracorporeal blood circuit that defines a lumen through which blood of a patient can flow;
an access device enabling the extracorporeal blood circuit to be connected to the patient;
first and second electrodes located within the lumen so as to contact blood flowing through the extracorporeal blood circuit, the first and second electrodes enabling an electrical signal to be injected into the extracorporeal blood circuit;
first and second coupling devices holding the first and second electrodes, respectively;
first and second contact members extending into the first and second coupling devices, respectively, to contact the first and second electrodes; and
electronics coupled operably to the first and second contact members outside the lumen, the electronics configured to apply a signal to the blood for monitoring the access device.

12. The extracorporeal blood system of claim 11, wherein the first and second coupling devices are used for connecting respectively to first and second tubes of the extracorporeal circuit.

13. The extracorporeal blood system of claim 11, the electronics being a first electronics, and which includes a third electrode located in the lumen, the third electrode placed in operable communication with second electronics configured to sense the signal applied to the blood for monitoring the access device.

14. The extracorporeal blood system of claim 11, wherein the first and second electrodes are placed in the lumen so as to form an electrical bypass between the patient and at least one of: an air trap, a dialyzer and a portion of the extracorporeal blood circuit operating with a blood pump.

15. The extracorporeal blood system of claim 11, wherein the extracorporeal circuit defining the lumen includes arterial and venous lines, and wherein the access device includes first and second needles connected to the arterial and venous lines.

16. An extracorporeal blood system comprising:
an extracorporeal blood machine including an extracorporeal blood circuit;
an access device enabling the extracorporeal blood circuit to be connected to a patient;
first and second coupling devices for connecting respectively to first and second tubes of the extracorporeal circuit, the first and second coupling devices each including an opening;
first and second electrodes held by the first and second coupling devices so as to contact blood flowing through the extracorporeal blood circuit, the first and second electrodes enabling an electrical signal to be injected into the extracorporeal blood circuit;
first and second contact members contacting the first and second electrodes through the respective openings of the first and second coupling devices; and electronics coupled operably to the first and second contact members for applying the electrical signal, the signal used to monitor the access device.

17. The extracorporeal blood system of claim 16, wherein at least one of the first and second openings extends at least substantially perpendicularly from at least of the first and second contact members, respectively.

18. The extracorporeal blood system of claim 16, wherein at least one of the electrodes and the contact members is sealed within the respective first and second coupling devices.

* * * * *

UNITED STATES PATENT AND TRADEMARK OFFICE
CERTIFICATE OF CORRECTION

PATENT NO. : 8,137,300 B2
APPLICATION NO. : 12/727993
DATED : March 20, 2012
INVENTOR(S) : Han et al.

It is certified that error appears in the above-identified patent and that said Letters Patent is hereby corrected as shown below:

In Claim 5, Column 15, Line 58, replace "devices respectively" with --devices, respectively--.

In Claim 10, Column 16, Line 6, replace "includes" with --include--.

In Claim 17, Column 17, Line 6, replace "from at least of the" with --from at least one of the--.

Signed and Sealed this
Twenty-fourth Day of July, 2012

David J. Kappos
*Director of the United States Patent and Trademark Office*